United States Patent
Wong et al.

[11] Patent Number: 5,985,324
[45] Date of Patent: Nov. 16, 1999

[54] FLOW CONTROLLER CONFIGURATIONS FOR AN ACTIVE AGENT DELIVERY DEVICE

[75] Inventors: Patrick S.-L. Wong, Burlingame; Vincent J. Ferrari, Foster City; Jeffrey W. Etter, Castro Valley; Miriam A. Martin, Los Altos; Nathan Roth, San Francisco; Christopher M. G. Ohms, San Mateo; Andrew I. Poutiatine, Menlo Park; James Horvath, San Jose, all of Calif.

[73] Assignee: ALZA Corporation, Palo Alto, Calif.

[21] Appl. No.: 09/073,982

[22] Filed: May 7, 1998

Related U.S. Application Data

[60] Provisional application No. 60/046,736, May 16, 1997.

[51] Int. Cl.$^6$ ........................................................ A61K 9/24
[52] U.S. Cl. .......................... 424/473; 424/438; 424/451; 424/464
[58] Field of Search ..................................... 424/473, 438, 424/451, 464

[56] References Cited

U.S. PATENT DOCUMENTS

| | | | |
|---|---|---|---|
| 1,661,400 | 3/1928 | Yehle | 128/222 |
| 2,436,505 | 2/1948 | DuRall | 128/222 |
| 2,867,536 | 1/1959 | Mead et al. | 99/138 |
| 3,409,224 | 11/1968 | Harp et al. | 128/260 |
| 3,610,483 | 10/1971 | Visconti et al. | 222/478 |
| 3,845,770 | 11/1974 | Theeuwes et al. | 128/260 |
| 3,995,631 | 12/1976 | Higuchi et al. | 128/260 |
| 4,034,756 | 7/1977 | Higuchi et al. | 128/260 |
| 4,111,202 | 9/1978 | Theeuwes | 128/260 |
| 4,320,759 | 3/1982 | Theeuwes | 128/260 |
| 4,327,725 | 5/1982 | Cortese et al. | 128/260 |
| 4,449,983 | 5/1984 | Cortese et al. | 128/260 |
| 4,581,013 | 4/1986 | Allen | 604/78 |
| 4,765,989 | 8/1988 | Wong et al. | 424/473 |
| 4,792,333 | 12/1988 | Kidder | 604/83 |
| 4,981,468 | 1/1991 | Benefiel et al. | 604/83 |
| 5,094,861 | 3/1992 | D'Auguste et al. | 426/85 |
| 5,110,597 | 5/1992 | Wong | 424/438 |
| 5,123,915 | 6/1992 | Miller et al. | 606/234 |
| 5,222,940 | 6/1993 | Wilk | 604/77 |
| 5,223,259 | 6/1993 | Lackney | 424/435 |
| 5,391,381 | 2/1995 | Wong | 424/473 |
| 5,509,605 | 4/1996 | Cripe | 239/33 |
| 5,718,681 | 2/1998 | Manning | 604/56 |
| 5,780,058 | 7/1998 | Wong et al. | 424/473 |
| 5,910,321 | 6/1999 | Wong et al. | 424/473 |

FOREIGN PATENT DOCUMENTS

| | | |
|---|---|---|
| 1906964 | 2/1969 | Germany . |
| WO97/03634 | 2/1997 | WIPO . |

*Primary Examiner*—S. Mark Clardy
*Assistant Examiner*—Kathryne E. Shelborne
*Attorney, Agent, or Firm*—Andrea G. Reister; Howrey & Simon

[57] ABSTRACT

The present invention is directed to an oral active agent delivery system comprising improved flow controllers. A hollow tubular member (10) containing the active agent formulation and having a fluid passing controller (14) is placed at one end (16) into a fluid and at a second end (18) into a patient's mouth. The active agent is delivered when the patient sips on the end of the chamber. The improved controllers prevent leakage of the active agent formulation.

24 Claims, 6 Drawing Sheets

FLOW CONTROLLER CONFIGURATIONS FOR AN ACTIVE AGENT DELIVERY DEVICE

RELATED APPLICATION

This application claims the priority of provisional application Ser. No. 60/046,736 filed May 16, 1997, which is incorporated herein by reference.

FIELD OF THE INVENTION

The present invention relates to the oral delivery of a liquid dispersion of an active agent. More particularly, improved flow controller configurations are disclosed which prevent active agent formulation particles from slipping in between the controller and the inner wall of the tubular delivery device. The controllers of the present invention allow a liquid to pass through or around the controller to form a suspension or slurry of the active agent formulation while preventing the controller from becoming stuck within the delivery device during administration of the active agent. The controllers of the present invention also provide an indication of the amount of the dose administered. Improved controller retention structures are also disclosed.

BACKGROUND OF THE INVENTION

Tablets, capsules, caplets and many other types of devices have been used for oral delivery of active agents. These forms are relatively easy to manufacture and convenient for use in the hospital or other institutional settings or at home. Many different types of active agents have been incorporated into such dosage forms—ranging from analgesics to antibiotics to hormones.

There are patients that, because of age or infirmity, have difficulty swallowing solid oral dosage forms. According to Kikendall et al., *Digestive Diseases and Sciences* 28:2 (1983), there were 221 cases documented between 1970–1982 of tablet and capsule induced oesophageal injury. The most commonly implicated drugs were tetracycline (108 cases), emepromium bromide (36 cases), potassium chloride (16 cases) and ferrous salts (12 cases).

In view of the above, there exists a need for oral dosage forms where swallowing of a large solid system is avoided that are easy to use and manufacture.

U.S. Pat. No. 2,436,505 to DuRall describes a pill doser for administering medicines in liquid form or in pills or tablets. The device has a bowl at the top for containing the medicine and a tube that can be submerged in a liquid held in a drinking glass. The liquid is drawn upward for administering the liquid and any pill or tablet present in the bowl.

U.S. Pat. No. 2,867,536 to Mead et al. describes an improved drinking straw where a soluble flavoring material is contained within an annular space contained within an inner and an outer tube. The inner tube has a bore through which liquid can be drawn. During use, the upper and lower caps are removed, the flavoring material emptied into the liquid and the flavored liquid drawn up through the inner tube and into the mouth.

U.S. Pat. No. 3,610,483 to Visconti describes a dispensing device for liquid medication that is formed in the shape of a straw. A predetermined dose of liquid medication is loaded into the straw which is then capped at both ends until the medication is dispensed when a patient removes the caps and sucks air into the device.

U.S. Pat. No. 4,581,013 to Allen is directed to a doser for orally administering a medication. A tube with a removable closure and a radially extending plate supports a solid medication and permits passage of a stream for liquid. The tube is fitted on top of a straw that is placed into a liquid.

U.S. Pat. No. 4,792,333 to Kidder describes a tamper proof package for containing and orally administering a solid substance. A tube has two portions that are separated by a supporting and confining means that supports and confines the solid substance but permits fluid flow. The ends of the tube are hermetically sealed.

U.S. Pat. No. 4,981,468 to Benefiel et al. is directed to a unit dosage form for delivering a therapeutic agent in free-flowing form. A slanted grid supports the dose between two ends of a tube.

Published PCT Application WO 97/03634 to Wong et al. describes an oral active agent delivery system comprising a hollow chamber that contains discrete units of active agent. A fluid passing retainer prevents release of the discrete units but permits fluid entry into the chamber. The retainer is transportable with the fluid entering the system.

A variety of other oral delivery systems have been described. These include a medicated pacifier (U.S. Pat. No. 5,123,915 to Miller et al.) and a lollipop type device for a solid medicament (U.S. Pat. No. 5,223,259 to Lackney).

SUMMARY OF THE INVENTION

In one aspect, the present invention provides improved flow controllers for oral active agent delivery devices. The active agent is in the form of discrete units and is contained within the lumen of a hollow tubular active agent delivery device. The controllers prevent release of the discrete units from the first end of the delivery device and permit fluid to enter into the lumen to form a suspension or slurry while lifting the formulation up the lumen towards the second end of the tubular member to the point of drug delivery.

In another aspect, improved flow controller retention structures are provided which prevent the controller from exiting through either end of the delivery device and facilitate use of the device.

In still another aspect, an improved controller for an oral active agent delivery system for delivering discrete units of active agent formulation in admixture with a fluid is provided. The system comprises a hollow tubular member having a first end and a second end and containing an active agent formulation in the form of discrete units between the ends, the controller being located within the hollow tubular member and capable of permitting fluid entry into the tubular member while preventing release of the discrete units from the first end of the tubular member and being transportable toward said second end by the fluid entering the system, and the controller comprises a core of bonded fibers.

DESCRIPTION OF THE DRAWINGS

The figures are not drawn to scale, but are set forth to illustrate various embodiments of the invention. Like numbers refer to like structures.

FIGS. 6–11 are cross-sectional views of various embodiments of controller 14.

DETAILED DESCRIPTION OF THE INVENTION

Accordingly, one aspect of the present invention is directed to improved flow controllers for controlling the passage of fluid through or around the controller to form a suspension or slurry with an active agent formulation within an oral delivery system for delivering discrete units of the active agent formulation in admixture with a fluid. The system comprises a tubular member comprising a first end and a second end. The first end is suitable for placement in a liquid and the second end is suitable for placement in the mouth of a patient. The system further comprises a lumen that contains a therapeutically effective amount of an active agent in the form of discrete units. The controllers prevent release of the discrete units from the first end and permit fluid to enter into the lumen to form a suspension or slurry while lifting the formulation up the lumen towards the second end of the tubular member. According to this aspect of the invention, the controller comprises an exterior surface provided with at least one protrusion extending therefrom which provides discrete areas of contact between the controller and the tubular member to provide a desired amount of drag or friction.

Another aspect of the invention relates to improved controller retention structures provided at the first and/or second ends of the delivery device in order to provide that the controller is maintained within the delivery device. The retention structure at the second end of the device may be configured to facilitate use of the delivery device.

Definitions

The term “active agent” refers to an agent, drug, compound, composition of matter or mixture thereof which provides some pharmacologic, often beneficial, effect. This includes foods, food supplements, nutrients, drugs, vitamins, and other beneficial agents. As used herein, the terms further include any physiologically or pharmacologically active substance that produces a localized or systemic effect in a patient. The active drug that can be delivered includes antibiotics, antiviral agents, anepileptics, analgesics, anti-asthmatics, anti-inflammatory agents and bronchodilators, and may be inorganic and organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, polysaccharides, steroids, hypnotics and sedatives, psychic energizers, tranquilizers, anticonvulsants, muscle relaxants, antiparkinson agents, analgesics, anti-inflammatories, muscle contractants, antimicrobials, antimalarials, hormonal agents including contraceptives, sympathomimetics, polypeptides and proteins capable of eliciting physiological effects, diuretics, lipid regulating agents, antiandrogenic agents, leukotriene antagonists, antiparasitics, neoplastics, antineoplastics, hypoglycemics, nutritional agents and supplements, growth supplements, fats, ophthalmics, antienteritis agents, electrolytes and diagnostic agents. The invention is particularly suited for autoviral therapy particularly to the combination dose of protease inhibitors and nucleoside analogues for HIV treatment.

Examples of active agents useful in this invention include zafirlukast prochlorperazine edisylate, ferrous sulfate, aminocaproic acid, mecamylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-b-estradiol, ethinyl estradiol, ethinyl estradiol 3-methyl ether, prednisolone, 17-b-hydroxyprogesterone acetate, 19-nor-progesterone, norgestrel, norethindrone, norethisterone, norethiederone, progesterone, norgesterone, norethynodrel, aspirin, acetaminophen, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, calcium gluconate, ketoprofen, ibuprofen, cephalexin, erythromycin, haloperidol, zomepirac, ferrous lactate, vincamine, phenoxybenzamine, diltiazem, milrinone, captropril, mandol, guanabenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptyline, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozymin and leutinizing hormone.

The term “active agent formulation” intends the active agent(s) optionally in combination with pharmaceutically acceptable carriers and additional inert ingredients.

The term “discrete units” intends the active agent formulation in solid or particulate form, and includes active agent formulations in liquid form encompassed by a solid surface.

An “oral dosage form” as described herein is meant the active agent formulation when placed in a discrete unit that is capable of maintaining its physical configuration and chemical integrity while housed within the delivery device.

As used herein, the terms "therapeutically effective amount" or "therapeutically effective rate" refer to the amount or rate of the active agent needed to effect the desired pharmacologic, often beneficial result.

The term "controller" refers to a plug or the like that allows for passage of fluids but does not allow for passage of other ingredients such as the active agent formulation that is contained in the delivery device.

The dispensing devices of the invention find use where it is inconvenient or unsafe to use solid oral dosage forms such as capsules or tablets. The devices may be particularly useful in geriatric or pediatric patient populations but they may also be useful for those who have difficulty swallowing capsules or tablets. A single delivery device or several devices can be administered to a patient during a therapeutic program.

This invention comprises the following features, either alone or in combination with each other:

An improved controller for an oral active agent delivery system for delivering discrete units of active agent formulation in admixture with a fluid comprising a hollow tubular member having a first end and a second end and containing an active agent formulation in the form of discrete units between the ends, the controller being located within the hollow tubular member and being capable of permitting fluid entry into the tubular member while preventing release of the discrete units from the first end of the tubular member and being transportable toward the second end by the fluid entering the system. The controller comprises an exterior surface provided with at least one protrusion extending therefrom which provides a discrete area(s) of contact between the controller and the tubular member.

The controller may comprise a cylindrical body portion provided with at least one protrusion on its exterior surface wherein the protrusion prevents leakage of the active agent from the first end of the device. The protrusion may comprise at least one ridge extending outwardly from and along the circumference of the cylindrical body portion wherein the ridge comprises a continuous spiral ridge extending outwardly from the exterior surface of the cylindrical body portion. The ridge may be at an acute angle or perpendicular to the longitudinal axis of the cylindrical member.

The controller may be fabricated with at least one longitudinal channel formed in the exterior surface of the cylindrical body portion to allow passage of fluid across the controller.

A groove may be provided in the cylindrical body portion along the circumference of the exterior surface and an O-ring positioned within the groove.

A groove in the cylindrical body portion may comprise retaining ridges and a flanged ring positioned within the groove and secured by the retaining ridges.

A hollow cap may be provided covering one end of said cylindrical body portion.

The controller may comprise at least one vertical fin extending from a central, cylindrical portion of the controller along its length. The fin may be rectangular or have a wave shaped exterior surface and may be provided with at least one recess along the exterior surface thereof.

A flexible circular member may be provided at one end of the controller, the diameter of the circular member being substantially the same or larger than that of the inner diameter of the tubular member.

Figure 1:
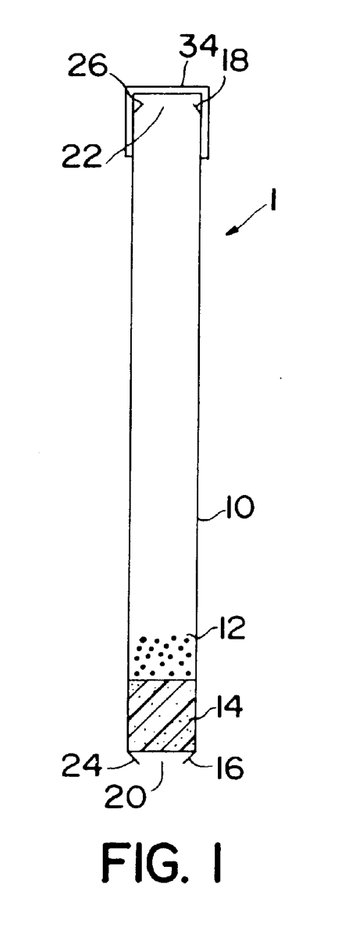
FIG. 1 is a cross-sectional view of one embodiment of the delivery device of the invention in prepared form prior to placement in a liquid medium.
Figure 2A:
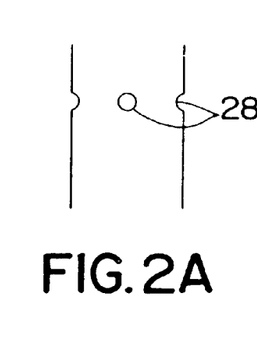
FIGS. 2A–2C are cross-sectional views of various controller retention structures according to the invention.
Figure 2B:
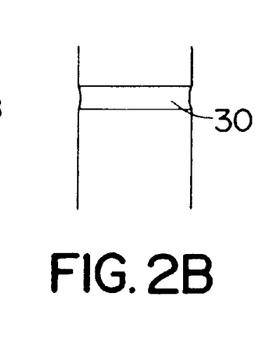
Figure 2C:
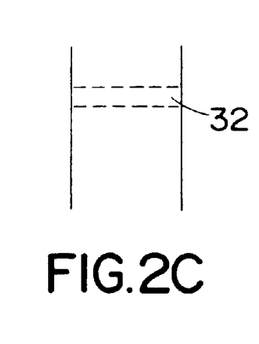
Figure 3A:
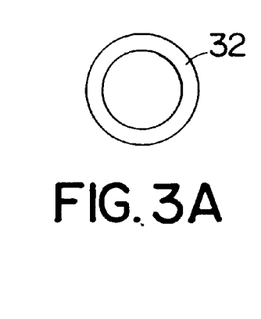
FIGS. 3A–3C are top views of various embodiments of the retaining means 32 depicted in FIG. 2C.
Figure 3B:
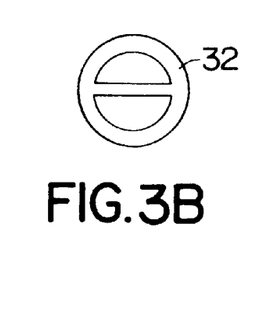
Figure 3C:
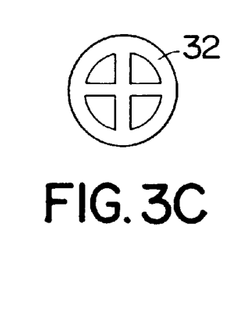

The invention will now be described with reference to the accompanying drawings. FIG. 1 depicts, in a cross-sectional view, one embodiment of the delivery device according to the invention. The device is in prepared form prior to placement in a fluid. Dispensing device 1 is shown in FIG. 1 to comprise an elongate tubular member 10 with a first end 16 and a second end 18. Contained within tubular member 10 is a lumen that contains an active agent formulation 12 and a controller 14. Active agent formulation 12, which can be particles of drug, coated drug particles, or "tiny time pills", either alone or with additional carriers, is placed in the tubular member 10. The tubular member 10 comprises a retaining means such as a restriction 24 to prevent controller 14 from exiting through the first end 16. The cross-section of opening 20 is smaller than that of the controller 14. In the embodiment shown in FIG. 1, the retaining means is made by crimping the end 16 of tubular member 10. Any convenient means that prohibits controller 14 from exiting through first end 16 while permitting passage of fluid is contemplated by this invention such as, without limitation, a series of dimples 28 or a continuous indentation 30 formed near one or both ends of the tubular member 10 as shown in FIGS. 2A and 2B, respectively. In another embodiment depicted in FIG. 2C, retaining means 32 is positioned at one or both ends of tubular member 10 for preventing controller 14 from exiting tubular member 10. The retaining means 32 may be as depicted in FIGS. 3A–3C, however, any element is contemplated that will allow passage of fluid without permitting passage of controller 14.

Figures 4A, 4B, 4C, 5, 6A, 6B:
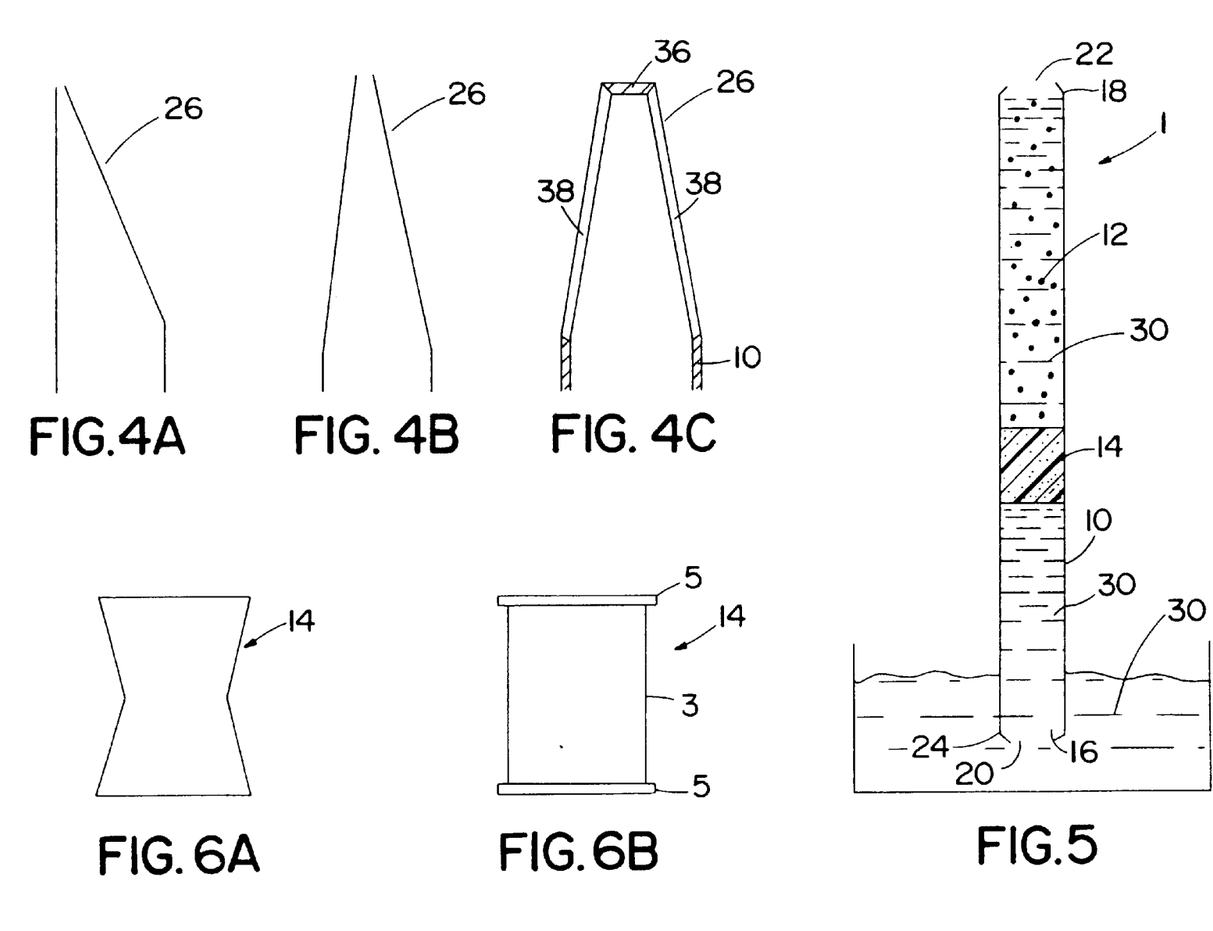
FIGS. 4A–4C are cross-sectional views of various embodiments of second end 18 of the device of FIG. 1.
FIG. 5 shows the device of FIG. 1 following placement in a liquid medium and delivery of a portion of the active agent formulation.

Second end 18 of tubular member 10 also has a retaining means 26 for preventing release of controller 14. In the embodiment shown in FIG. 1, the retaining means 26 is prepared by crimping the end 18 of tubular member 10. Preferably, retaining means 26 is configured to facilitate sucking of the active agent formulation 12 into the mouth of the user as shown in FIGS. 4A and 4B. According to another preferred embodiment depicted in FIG. 4C, tubular member 10 gradually tapers to a reduced diameter top portion 36 at the second end thereof. Side exit openings 38 are provided along tapering region and allow the active agent formulation 12 to be administered to the patient while preventing controller 14 from exiting tubular member 10. End-cap 34 is placed over the second end 18 of the tubular member 10 prior to use to prevent release of the active agent formulation 12.

FIG. 5 shows the delivery device 1 in operation after having been placed in fluid 30. The first end 16 of the delivery device 1 is placed in the fluid 30 and the second end 18 of the device is placed in the patient's mouth after removing cap 34. It is preferable to place the device 1 into the container holding fluid 30 prior to removing cap 34. The patient sips on the second end 18 of the device and an admixture of fluid 30 and active agent formulation 12 is delivered through opening 22 and into the patient's mouth.

FIGS. 6–11 depict various embodiments of the improved flow controllers 14 of the present invention. Controllers 14 are designed to allow a predetermined amount of drug to move up through tubular element 10 to the point of delivery at the second end 18. The controller 14 is configured to allow liquid to pass either through or around the controller without allowing active agent formulation 12 to slip between the sides of controller 14 and the inner wall of tubular member 10 or to leak through the porosity of controller 14 towards first end 16. According to another embodiment, it is preferable that controller 14 is adapted to accommodate a variation in part sizes such as the inner diameter of tubular member 10. This is accomplished through the selection of materials for controller and/or by providing controller 14 with protrusions such as fins, ridges, or rings which act as a seal. The protrusions also create friction or drag between controller 14 and tubular member 10 to allow time for the liquid to mix with the active agent formulation 12 after passing though or around controller 14.

With reference to the drawings, FIG. 6A depicts one embodiment of controller 14 wherein controller 14 is a solid foam plug having an hourglass shape. FIG. 2B is also a solid foam plug with a central section 3 having a smaller diameter than top and bottom sections 5 in order to form a spool design. In each of these embodiments, the upper and lower sections are of a greater diameter than the middle section and create friction or drag between controller 14 and tubular member 10 to allow time for the liquid to mix with the active agent formulation 12 and act as a seal to prevent any backflow of active agent.

Figure 7A:
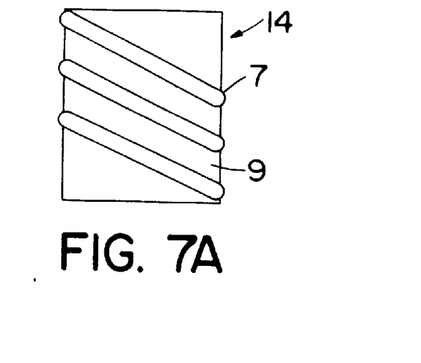
Figure 7B:
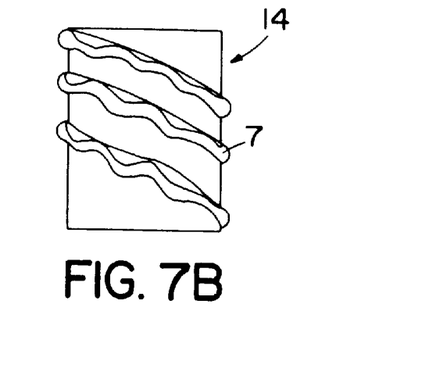

FIGS. 7A–7D are cross-views of another embodiment of controller 14 of the present invention. In these embodiments, a spiral ridge 7 runs along the outer surface of cylindrical plug member 9. The spiral ridge 7 may be a continuous spiral or a plurality of parallel ridges and may be fabricated separately or together with the cylindrical plug member 9. Spiral ridge 7 may be of varying thickness and configurations and preferably forms an acute angle with the longitudinal axis of cylindrical plug member 9. For example, the spiral ridge may be provided a wavy ridge as shown in FIG. 7B in order to provide desired flow characteristics of the liquid as it passes through controller 14 before mixing with the active agent formulation 12.

Figure 7C:
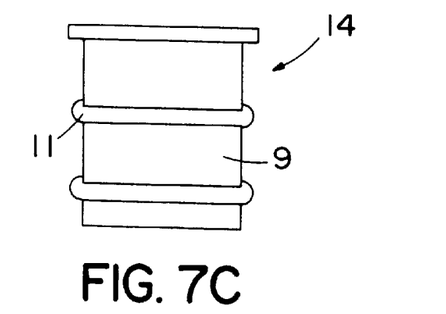
Figure 7D:
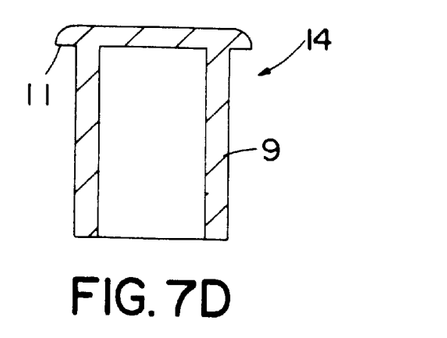
Figure 7E:
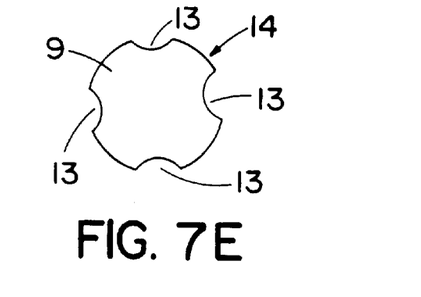
FIGS. 7E and 8E are top views of the controllers depicted in FIGS. 7A and 8A, respectively.

In another embodiment depicted in FIG. 7C, the cylindrical plug member 9 is provided with a number of horizontal ribs 11 preferably 1–4. According to this embodiment, cylindrical member 9 may be solid or hollow as seen in FIG. 7D Additionally, the plug member 9 of FIGS. 7A–7D may be provided with flow through channels 13 as depicted in FIG. 7E (top view) so that liquid may be drawn up through channels 13 and past controller 14 to mix with the active agent formulation 12. The size of the channels 13 is selected to allow liquid to be drawn up through controller 14 but not so large as to allow active agent formulation to pass through controller 14.

Figure 8A:
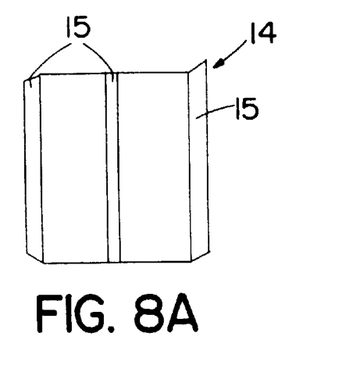
Figure 8B:
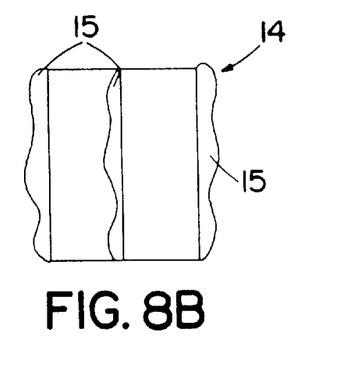
Figure 8C:
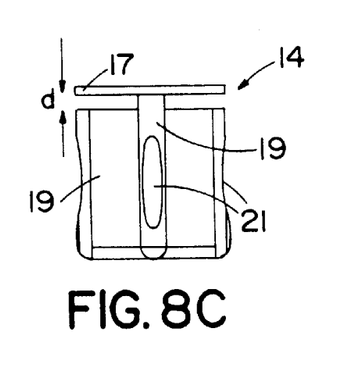
Figure 8D:
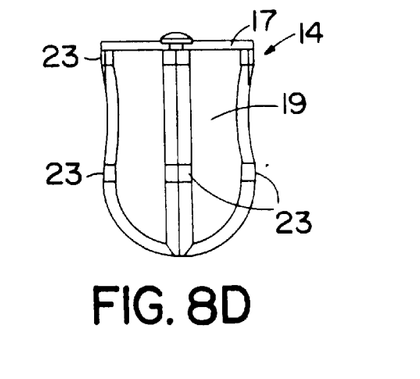

FIGS. 8A and 8B depict another embodiment wherein controller 14 comprises a number of vertical fins 15, preferably from 2–10 rectangular fins. As seen in FIG. 8B, the fins may be wavy in order to provide for more turbulent flow of liquid as it passes around the fins 15 before mixing with the active agent formulation 12. According to yet another embodiment, controller 14 may be a molded finned controller as depicted in FIGS. 8C and 8D formed from a non-porous, preferably thermoplastic material. As seen in FIG. 8C, controller 14 comprises circular top 17 from which fins 19 extend downwardly therefrom. Top 17 is a flexible member capable of flexing in a direction away from fins 19 so as to allow fluid to pass around top 17 and tubular member 10 and may be provided as a separate element. Fins 19 also act as a support to prevent flexing of top 17 in a direction towards fins 19 so as to prevent active agent formulation from passing around controller 14 and out first end 16.

Figure 8E:
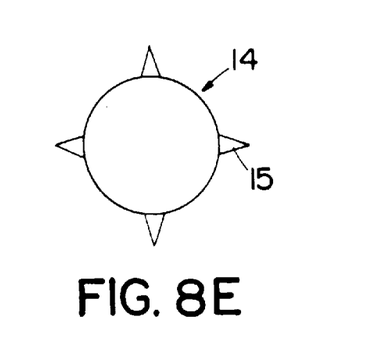

As seen in FIG. 8C gap d may be provided between some or all of the fins 19 and top 17. Additionally, recesses 21 may be provided along the edge of the fins 19 in order to provide the desired amount of contact between controller 14 and the inner surface of tubular member 10. FIG. 8D depicts another embodiment wherein the fins 19 are rounded at the bottom to meet at a single point. Areas 23 indicate the point of contact between the controller 14 and tubular member 10. FIG. 8E is a top view of the controller of FIG. 8A.

Figure 9A:
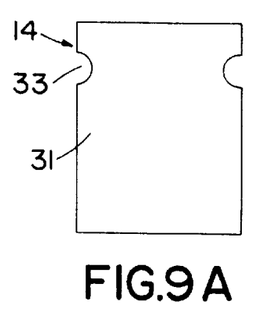
Figure 9B:
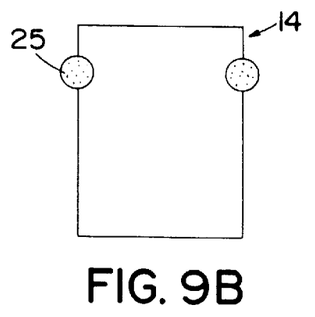
Figure 9C:
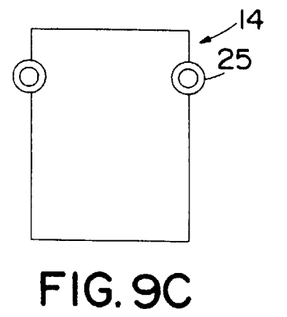
Figure 10A:
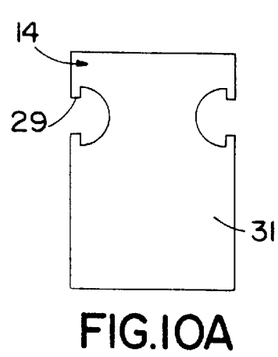
Figure 10B:
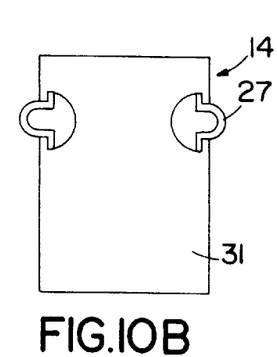
Figure 10C:
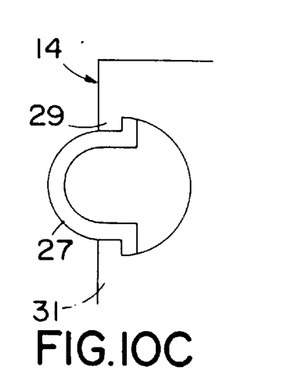

FIGS. 9–10 depict other embodiments of the controller of the present invention which comprise an O-ring 25 or flanged ring of material 27 which provide controller 14 with a seal against the inner wall of tubular member 10. FIG. 9A shows the controller body 31 including annular groove 33 to receive O-ring 25 therein. As seen in FIGS. 9B and 9C, O-ring 25 may be a solid or hollow, tubular ring of material. Alternatively, as seen in FIGS. 10A–10C, controller 14 may be formed to include ridges 29 which act to retain flanged ring 27 in position on the controller 14. O-ring 25 and flanged ring 27 prevent the active agent formulation 12 from passing between controller 14 and the inner wall of tubular member 10, thus preventing the controller 14 from getting stuck as it moves within tubular member 10. Further, rings 25 and 27 allow the outer diameter of controller 14 to vary slightly to accommodate differing diameters encountered within tubular member 10.

Figure 11A:
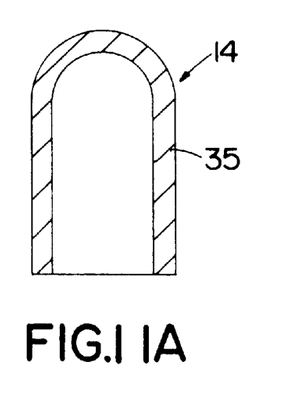
Figure 11B:
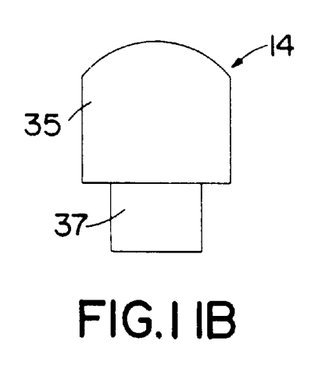
Figure 11C:
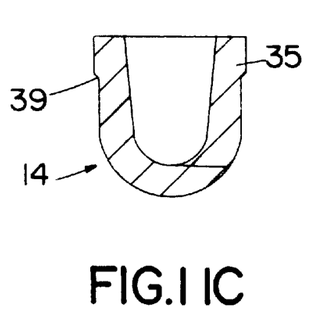

In the embodiment shown in FIGS. 11A–11C, controller 14 is provided as a hollow cap. The hollow cap controller 35 may be designed to function as a controller by itself, or may placed over a hollow or solid cylindrical plug member 37 to form the plug cap depicted in FIG. 11 B. Other hollow cap designs are depicted in FIG. 11 C wherein cap 35 comprises stepped flange 39 at its open end to provide the desired contact with tubular member 10.

Figure 12:
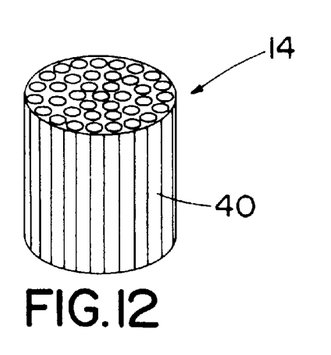
FIG. 12 is a perspective view of another embodiment of the invention wherein the controller is formed from a plug of bonded fibers.

As illustrated in FIG. 12, the controller 14 may be fabricated as a plug of bonded fibers 40. The fibers may be bonded by conventional means such as by intertwining or weaving of the fibers or portions thereof, by the application of heat, causing at least a portion of the outer surfaces of the fibers to attach to each other, and the like. For ease of manufacture, the controller 14 is typically formed as a cylinder. The plug of bonded fibers 40 is compressible and may be manufactured with a diameter slightly greater than the inner diameter of tubular member 10. When seated within the tubular member 10, the controller 14 will seal to prevent release of discrete units from the first end of the tubular member 10, yet permit fluid to enter the lumen to transport the active agent to the second end and to the patient. The fiber plug is also transportable with the fluid to the second end of the tubular member upon application of suction to the second end of the tubular member. While not shown, the external surfaces of the fiber plug may be modified as described herein to provide various configurations for sealing between the outer surface of the controller and the inner surface of the tubular member.

The controller 14 serves as a one-way valve and may be formed from porous or non-porous materials. When suction is applied through the tubular member 10, the controller 14 is deformed, thereby permitting fluid to flow around and/or through the controller 14. When suction is removed, the controller 14 relaxes and automatically seals the tubular member 10. The controller 14 also can move up the elongated tubular member, thereby aiding in delivery of the active agent formulation 12. The position of controller 14 in tubular member 10 serves as an indicator of approximately how much of the active agent formulation 12 has actually been delivered. The controller permits the free flow of liquid medium but prohibits passage of the active agent formulation from the device prior to delivery.

The controller 14 may be prepared from thermoplastic materials and low or high density foam materials known in the art such as, without limitation, ethylene vinyl acetate copolymers and polyolefins such as, for example, polyethylene, polypropylene and the like, and may be a low density, closed cell foam.

Also, as described above, the controller 14 may be fabricated as a deformable and/or porous plug of bonded fibers, preferably in the shape of a cylinder, with or without modification of the external surface of the controller. The controller 14 may be formed as a bonded fiber cylinder of polymeric fibers, such as, polyolefin fibers, with or without a polyester core, having a fiber diameter of between 0.25 and 0.35 inches and a fiber length of between 0.25 and 0.4 inches, preferably a diameter between 0.280 and 0.310 inches and a length between 0.300 and 0.320 inches. The plug will generally be fabricated with a diameter that is slightly larger than the inner diameter of the tubular member 10 such that it will be slightly compressed within the tubular member 10, but not so tightly compressed that fluid does not flow through and/or around the controller upon the application of suction. Examples of useful polyolefins include low density polyethylene (LDPE), high density polyethylene (HDPE), ultra high molecular weight polyethylene (UWMW) and polypropylene. Presently preferred fiber materials include polypropylene fibers obtained from American Filtrona Corporation and those having a polyester core with a polyolefin sheath obtained from Porex Technologies, Fairburn, Ga. Other materials that may be use to fabricate the fiber plug controller include polyesters, cellulose acetate, nylon, felt, and cotton. Generally hydrophobic materials are preferred, whether intrinsically hydrophobic or modified to be hydrophobic by the addition of surfactants and the like. Substantially cylindrical fiber plugs provide controllers having the desirable sealing characteristics set forth herein and permit the flow of fluid to deliver the active agent formulation as described. Such fiber plugs may be fabricated with or without the surface modifications of the controllers described herein.

The active agent itself may be in liquid, solid, or semisolid form. The active agent formulation that contains the active agent may contain additional material such as binders, coating materials, or stabilizers such that the formulation is formed into one or more discrete units. The units may also be mixed with sugar granules and flavoring agents to enhance ingestion. The discrete units may be designed in a multitude of ways to provide a specific drug delivery profile. One embodiment comprises a formulation that is in particulate form. These particulates are generally between about 50 and 2000 $\mu$m in diameter, usually between about 100–500 $\mu$m in diameter. Where the particulate has an unpleasant taste, the particulate may be taste masked by methods that are well known in the art. For example, the particulate may be mixed with effervescent materials (acid and carbonate sources) to form a free flowing mixture. The particulates may be designed to provide immediate delivery of the active agent, they may be coated to provide for prolonged release or delayed pulse release of the active agent, or they may be designed to provide for a combination of immediate, pulsed and/or prolonged delivery of active agent. The particulates may be coated with an enteric coating to provide for targeted release of the active agent. In addition there may be active agent formulations that contain more than one active agent.

In other embodiments, the active agent may be in the discrete units in liquid form contained, for example, within soft gelatin capsules or microcapsules, or within a solid oral dosage form. These dosage forms may include, matrix or other types of tablets, pellets and elongated tablets where the height to diameter ratio exceeds one, capsules, elementary osmotic pumps, such as those described in U.S. Pat. No. 3,845,770, mini osmotic pumps such as those described in U.S. Pat. Nos. 3,995,631, 4,034,756, and 4,111,202, and multichamber osmotic systems referred to as push-pull and push-melt osmotic pumps, such as those described in U.S. Pat. Nos. 4,320,759, 4,327,725, 4,449,983, and 4,765,989 all of which are incorporated herein by reference.

It is to be understood that more than one active agent may be incorporated into the active agent formulation in a device of this invention, and that the use of the term "agent" in no way excludes the use of two or more such agents.

The agents can be in various forms, such as soluble and insoluble charged or uncharged molecules, components of molecular complexes or nonirritating, pharmacologically acceptable salts.

The amount of active agent employed in the delivery device will be that amount necessary to deliver a therapeutically effective amount of the agent to achieve the desired result. In practice, this will vary widely depending upon the particular agent, the severity of the condition, and the desired therapeutic effect. However, the device is generally useful for active agents that must be delivered in fairly large doses of from about 100 mg to 5000 mg, usually in the range of from about 250 mg to about 2500 mg. However, since the devices may also be useful in pediatric patients, doses in the ranges of 25 to 250 mg are also contemplated herein.

Representative materials for forming devices including the elongated tubular member, the end caps and tabs, include, without limitation, paper, plastic such as propylene/styrene copolymers, polypropylene, high density polyethylene, low density polyethylene and the like. The devices usually have an inner diameter of between about 3 and 8 mm and a wall thickness of between about 0.1 and 0.4 mm. The devices are between about 10 and 30 cm in length.

The fluid that is used for suspending the active agent formulation by sipping through the active agent formulation chamber is preferably any good-tasting liquid including but not limited to water, juice, milk, soda, coffee, tea etc. Care must be taken to ensure compatibility of the fluid with the active agent formulation.

The above description has been given for ease of understanding only. No unnecessary limitations should be understood therefrom, as modifications will be obvious to those skilled in the art.

We claim:

1. An improved controller for an oral active agent delivery system for delivering discrete units of active agent formulation in admixture with a fluid, said system comprising a hollow tubular member, said tubular member having a first end and a second end and containing an active agent formulation in the form of discrete units between said ends, said controller being located within said hollow tubular member and capable of permitting fluid entry into the tubular member while preventing release of the discrete units from the first end of the tubular member and being transportable toward said second end by the fluid entering the system, said controller comprising an exterior surface provided with at least one protrusion extending therefrom, said protrusion providing discrete areas of contact between the controller and the tubular member.

2. The controller of claim 1 wherein said controller comprises a cylindrical body portion provided with said at least one protrusion on its exterior surface wherein said protrusion prevents leakage of said active agent from said first end of the device.

3. The controller of claim 2 wherein the protrusion comprises at least one ridge extending outwardly from and along the circumference of the cylindrical body portion.

4. The controller of claim 3 wherein the ridge comprises a continuous spiral ridge extending outwardly from the exterior surface of the cylindrical body portion.

5. The controller of claim 3 wherein the ridge is perpendicular to the longitudinal axis of the cylindrical member.

6. The controller of claim 5 further comprising at least one longitudinal channel formed in the exterior surface of the cylindrical body portion to allow passage of fluid across the controller.

7. The controller of claim 3 wherein the cylindrical body portion comprises a groove along the circumference of the exterior surface and the ridge comprises an O-ring positioned within the groove.

8. The controller of claim 3 wherein the cylindrical body portion comprises a groove comprising retaining ridges and the ridge is a flanged ring which is positioned within the groove and secured by the retaining ridges.

9. The controller of claim 3 wherein the ridge forms an acute angle with the longitudinal axis of the cylindrical member.

10. The controller of claim 2 wherein the protrusion comprises a hollow cap covering one end of said cylindrical body portion.

11. The controller of claim 1 wherein the controller comprises a central portion and the protrusion comprises at least one vertical fin extending from the central portion along its length.

12. The controller of claim 11 wherein the central portion comprises a cylindrical body portion.

13. The controller of claim 11 wherein the at least one fin is rectangular.

14. The controller of claim 11 wherein the at least one fin is provided with at least one recess along the exterior surface thereof.

15. The controller of claim 11 wherein the at least one fin comprises a wave shaped exterior surface.

16. The controller of claim 11 further comprising a flexible circular member at one end of the controller, the diameter of said circular member being substantially the same or larger than that of the inner diameter of the tubular member.

17. The controller of claim 1 wherein the controller is formed from a thermoplastic material.

18. The controller of claim 17 wherein the thermoplastic material is selected from ethylene vinyl acetate copolymers, polyethylene, and polypropylene.

19. The controller of claim 1 wherein the controller is formed from a high or low density foam.

20. The controller of claim 19 wherein the controller is formed from a closed cell foam.

21. The controller of claim 20 wherein the controller is formed from low density closed cell polyethylene.

22. An improved controller for an oral active agent delivery system for delivering discrete units of active agent formulation in admixture with a fluid, said system comprising a hollow tubular member, said tubular member having a first end and a second end and containing an active agent formulation in the form of discrete units between said ends, said controller being located within said hollow tubular member and capable of permitting fluid entry into the tubular member while preventing release of the discrete units from the first end of the tubular member and being transportable toward said second end by the fluid entering the system, said controller comprising a plug of bonded fibers.

23. The controller of claim 22 wherein the fibers comprise a polyolefin fiber, optionally having a polyester core.

24. The controller of claim 23 wherein the fibers comprise a fiber having a polyester core and a polyethylene sheath.

* * * * *